(12) United States Patent
Kumar et al.

(10) Patent No.: US 8,668,938 B2
(45) Date of Patent: Mar. 11, 2014

(54) COMPOSITION AND MANUFACTURING PROCESSES OF A TOXICITY FREE BOTANICAL DRUG FOR CURATIVE TREATMENT OF CHRONIC DISEASES

(75) Inventors: Ashok Kumar, Aligarh (IN); Aditi Kumar, Aligarh (IN); Prakrati Kumar, Aligarh (IN); Priti Kumar, Aligarh (IN)

(73) Assignee: Ashok Kumar, Aligarh (IN)

( * ) Notice: Subject to any disclaimer, the term of this patent is extended or adjusted under 35 U.S.C. 154(b) by 0 days.

(21) Appl. No.: 13/575,807

(22) PCT Filed: Jan. 29, 2010

(86) PCT No.: PCT/IN2010/000051
§ 371 (c)(1),
(2), (4) Date: Oct. 11, 2012

(87) PCT Pub. No.: WO2011/092712
PCT Pub. Date: Aug. 4, 2011

(65) Prior Publication Data
US 2013/0028993 A1    Jan. 31, 2013

(51) Int. Cl.
*A01N 65/00*    (2009.01)

(52) U.S. Cl.
USPC .......................................................... 424/725

(58) Field of Classification Search
None
See application file for complete search history.

(56) References Cited

U.S. PATENT DOCUMENTS

| 5,602,103 A | 2/1997 | Sugiura et al. |
| 2006/0039998 A1 | 2/2006 | Ohnogi et al. |
| 2009/0263514 A1 | 10/2009 | Gopinathan |

OTHER PUBLICATIONS

Hosseinzadeh, H. et al., "Protective effect of aqueous saffron extract (*Crocus sativus* L.) and crocin, its active constituent, on renal ischemia-reperfusion-induced oxidative damage in rats," J. Pharm. Pharmaceut. Sci., (2005) vol. 8, No. 3, pp. 387-393.

Sun et al., "Chemical Constituents of *Crinum asiaticum* L. var. sinicum Baker and Their Cytotoxic Activities," Chemistry & Biodiversity, (2009), vol. 6, pp. 1751-1757.

Akhondzaeh, S. et al., "A 22-week, multicenter, randomized, double-blind controlled trial of *Crocus sativus* in the treatment of mild-to-moderate Alzheimer's disease," Psychopharmacology, (2010), vol. 207, pp. 637-643.

Agha-Hosseini, M. et al., "*Crocus sativus* L. (saffron) in the treatment of premenstrual syndrome: a double-blind, randomised and placebo-controlled trial," BJOG, (2008), vol. 115, pp. 515-519.

Ghazavi, A. et al., "Effect of Ethanol Extract of Saffron (*Crocus sativus* L.) on the Inhibition of Experimental Autoimmune Encephalomyelitis in C57bl/6 Mice," Pakistan Journal of Biological Sciences, (2009), vol. 12, No. 9, pp. 690-695.

Abdullaev, F.I. et al., "Biomedical properties of saffron and its potential use in cancer therapy and chemoprevention trials," Cancer Detection and Prevention, (2004), vol. 28, pp. 426-432.

Kim, Y.H. et al., "Anti-inflammatory activity of *Crinum asiaticum* Linne var. *Japonicum* extract and its application as a cosmeceutical ingredient," J. Cosmet. Sci., (Sep.-Oct. 2008), vol. 59, No. 5, pp. 419-430. (Abstract Only).

Min, B et al., "Inhibitory Effects of Korean Plants on HIV-1 Activities," Phytotherapy Res., (2001), vol. 15, pp. 481-486.

Samud A.M. et al., "Anti-inflammatory activity of *Crinum asiaticum* plant and its effect on bradykinin-induced contractions on isolated uterus," Immunopharmacology, (1999), vol. 43, pp. 311-316.

Wang, Y. et al., "Antidepressant properties of bioactive fractions from the extract of *Crocus sativus* L.," J. Nat. Med., (2010), vol. 64, pp. 24-30.

*Primary Examiner* — Michael Meller
(74) *Attorney, Agent, or Firm* — The Webb Law Firm

(57) ABSTRACT

This invention discloses composition and manufacturing processes of a toxicity free botanical drug formulation for curative treatment of chronic diseases. It is manufactured from plants *Crinum asiaticum* and *Crocus sativus*. This drug was administered to human volunteers by oral and intranasal routes in effective amount for an effective time period. Effective amount and effective time of administration varies from one human volunteer to another depending upon age, body weight, length of disease, severity of disease, type of the disease. In vitro experiments show that this botanical drug causes proliferation and differentiation of stem cells.

4 Claims, No Drawings

COMPOSITION AND MANUFACTURING PROCESSES OF A TOXICITY FREE BOTANICAL DRUG FOR CURATIVE TREATMENT OF CHRONIC DISEASES

OBJECTS OF THE INVENTION

The main object of this invention is to develop composition of a toxicity free botanical drug formulation for curative treatment of chronic diseases.

Other object is to develop composition of a toxicity free botanical drug formulation, which causes proliferation and differentiation of stem cells.

Further object of this invention is to develop composition and manufacturing processes of this toxicity free botanical drug formulation.

Another object of this invention is to develop methods of treatment of patients with this toxicity free botanical drug formulation so that they become completely free from chronic disease(s).

FIELD OF INVENTION

This invention relates to composition and manufacturing processes of a toxicity free botanical drug formulation from plants *Crinum asiaticum* and *Crocus sativus* for curative treatment of chronic diseases.

BRIEF DESCRIPTION OF THE INVENTION

According to this invention here is provided a toxicity free Botanical drug, its composition and manufacturing process(es) which curatively treats chronic diseases when an effective amount is administered to patients for effective time period, comprising of 0.01%-99.999% of *Crinum asiaticum* or component(s) thereof and 0.001%-30% of *Crocus sativus* or components thereof.

Toxicology

This botanical drug was administered to human volunteers for several years altogether, but no toxic effects were observed.

BACKGROUND OF THE INVENTION

Description of the Prior Art

Almost 50% of the world population suffers with one or the other chronic disease(s). Till date there is no cure available for any of the chronic diseases under any system of medical practice. All chronic diseases are crippling and lead to heavy burden on healthcare system, almost US$ 100 billion are spent per annum just to provide symptomatic relief to the patients, that too laden with toxicity. Till date medical system can only give symptomatic relief to a patient suffering with one or the other chronic disease(s). Patient has to use medicines which are very toxic. In the present invention, botanical drug is not only free of toxicity but is curative in nature. No recurrence of disease occurs even several years after stopping the treatment. Various chronic diseases are as follows, but this invention is not limited to these diseases only.

Rhinitis:

Rhinitis is a common chronic disease also identified as runny nose. In this disease nasal mucosa gets inflamed resulting in secretion of excessive mucous thus giving symptoms of runny nose, nasal congestion and post nasal drip. Prevention is the best measure to control Rhinitis. In case of Allergic Rhinitis avoidance of allergens and in case of Vasomotor Rhinitis avoidance of irritants can keep the symptoms under control. Rinsing of nasal cavity with salted water and taking steam are helpful. Antagonistic drugs, anti-leukotrienes, Glucocorticoids, Steroidal nasal sprays are used for control of Rhinitis. These medications have one or the other side effects, most notable is drowsiness and none of these treatments are curative. Patients have to use these medications life long and live with disease and drug toxicity.

Sinusitis:

Chronic Sinusitis is a disease condition in which paranasal sinuses are inflamed. It is classified into four types. Maxillary Sinusitis, Frontal Sinusitis, Ethmoid Sinusitis, Sphenoid Sinusitis. Sinusitis sometimes occurs with polyps. Symptoms of Sinusitis are facial pain, nasal congestion, thick yellow or green nasal discharge, headache, vertigo, feeling of facial fullness, general malaise, fever etc. Nasal irrigation with warm saline water is helpful in relieving the symptoms of Sinusitis. Acetoaminophen and Ibuprofen can be used to get relief from headache, pain, fever etc. Nasal corticosteroids are not very useful in Sinusitis. Thus in chronic Sinusitis surgery is advised. But none of these treatments are curative.

Asthma:

Asthma, a chronic disease caused by inflammation of the lungs in which bronchi are reversibly narrowed. In chronic obstructive pulmonary disease and chronic bronchitis inflammation is irreversible. In emphysema alveoli are inflamed. All these diseases show common symptoms such as night time cough, shortness of breath, tight feeling in the chest etc. An acute exacerbation of Asthma is also called as Asthma attack. Best way to prevent Asthma is avoidance of allergens and triggers such as household dust mites, grass pollen, perfumes, hair spray etc. Preventive medication for Asthma is allergen immunotherapy. For control of symptoms inhaled glucocorticoids, Leukotriene modifiers, mast cell stabilizers are mostly advised. Anticholinergics, Theophylline, Aminophylline, Antihistamines, Salbutamol, Methotrexate etc. are also useful in control of Asthma. But none of these medications provide complete freedom from the disease.

Urticaria:

Urticaria is a type of skin disease caused by an inflammatory reaction in the skin which results in edema notable as red, raised, itchy bumps. Different types of Urticaria include allergic Urticaria, non-allergic Urticaria, autoimmune Urticaria, chronic idiopathic Urticaria etc. Best way to control Urticaria is to avoid known allergens and stimulus. Usually antihistamines such as Diphenhydramine, Hydroxyzine, Cetrizine etc. are given to the patients. Drugs like Cimetidine, Ranitidine are also helpful. In severe cases oral corticosteroids are prescribed. None of these treatments are curative in nature, so patient has to live with disease and toxic side effects.

Psoriasis:

Psoriasis is a non-contagious skin disease which affects joints and nails also. This is an autoimmune disease causing inflammation in joints and on skin causing red scaly patches. Applying moisturizers and skin cream on affected areas helps in reducing inflammation and thus clearing the plaques. Creams and ointments containing coal tar, Dithranol, Corticosteroids etc. are routinely prescribed. Phototherapy and photochemotherapy is also advised in some cases. In severe cases Methotrexate, Retinoids etc. are given to the patients but none of these treatments are curative in nature.

Allergic Conjunctivitis:

Chronic allergic Conjunctivitis denotes the inflammation of the Conjunctiva, the outermost layer of the eye and the inner surface of eyelids. Common symptoms of Conjunctivitis are redness, irritation and watering of eyes. Frequent washing of face and eyes with cold water and artificial tears relieve discomfort in mild cases. In more severe cases antihistamines and non steroidal, anti-inflammatory agents are prescribed, but none is curative.

Eczema:

Eczema is a chronic disease due to inflammation of epidermis. Common symptoms are skin edema, redness, itching and dryness, crusting, flaking etc. Different types of Eczema are atopic Eczema, contact dermatitis, xerotic Eczema etc. Moisturizer is helpful in relieving symptoms of Eczema. Strong detergents and soaps should not be used on affected parts. Corticosteroids such as Hydrocortisone, Clobetasol propionate, Betamethasone valerate are prescribed for suppressing symptoms of Eczema. In severe cases oral corticosteroids such as Prednisolone or Triamcinolone injections are given to patients. But all these agents offer symptomatic relief only.

Vitiligo:

Vitiligo is a chronic disorder causing depigmentation of skin in patches. In this disease, the melanocytes are either dead or unable to make skin pigments. In mild Vitiligo patches can be hidden with makeup. Sunlight exposure is also useful sometimes as this may cause regeneration of melanocytes so they can produce pigments. Phototherapy with Psoralen is also helpful in some cases. Immunomodulator cream such as Protopic also causes repigmentation in some cases. Some patients opt for complete depigmentation. Physicians usually prescribe Cortisteroids. But none of these treatments are curative.

Food Allergy:

Food allergy is caused by an abnormal reaction to food substances. Mostly allergic reactions have an acute onset and results in symptoms such as skin rashes, nasal congestion, wheezing, shortness of breath, itching and swelling of lips, eyes, tongue, face, nausea vomiting, abdominal pain and rarely anaphylaxis which results in death. Avoidance of allergic food is the only way by which food allergy can be controlled. People diagnosed with food allergy are advised to carry an autoinjector of Epinephrine which can be injected in case of allergic reaction.

Diabetes:

Diabetes is a chronic disease in which body does not produce or respond to Insulin. Insulin is a hormone produced by pancreas which causes transfer of glucose in the cells so it can turn into energy. In diabetes this glucose accumulates in the blood and gets excreted in urine giving rise to various disease symptoms such as polyuria, polydipsia etc. Diabetes can be controlled by diet, exercise and weight loss. By use of various oral drugs and Insulin, it is treatable but there is no cure. Diabetes and its treatment causes complications such as hypoglycemia, diabetic ketoacidosis etc.

Arthritis:

Arthritis is a group of chronic diseases involving damage to the body joints. There are more then 100 types of Arthritis such as Osteoarthritis, Rheumatoid Arthritis, Psoriatic Arthritis, Gouty Arthritis, Pseudogout, juvenile idiopathic Arthritis, Still's disease, Ankylosing spondilitis, reactive Arthritis etc. Common symptoms of all Arthritis are inflammation and pain in affected joints. For people suffering with Arthritis physical therapy, exercise, weight control, pain relieving medicines, dietary supplements etc. are advised. Joint replacement surgery is also helpful but none of these treatments offer cure from the disease.

Hypertension:

Hypertension or high blood pressure is a disease condition in which blood pressure is chronically elevated. Continuous hypertension is one of the risk factors for stroke, heart attack, heart failure, chronic renal failure etc. Mild to moderate hypertension is usually asymptomatic but accelerated hypertension is associated with headache, confusion, nausea, vomiting etc. Best way to control hypertension is to change life style. Some of the changes are such as weight and stress reduction, reducing salt, sugar and fat intake etc. For chronic problem antihypertensive drugs are prescribed. Commonly prescribed drugs are ACE inhibitors such as fosinopril, captopril etc., calcium channel blockers such as amlodipine, diltiazem etc., diuretics such as chlortalidone etc. But none of these drugs offer cure from disease.

Angina Pectoris:

Angina pectoris is caused because of lack of blood and hence oxygen supply to the heart muscles resulting in pain, heaviness, tightness etc. in chest. Apart from chest discomfort angina pain may also be experienced in back, abdomen, neck, jaws etc. Coronary artery disease is the main cause of Angina. Major risk factors for Angina are hypertension, high cholesterol, physical and emotional stress etc. Usually it lasts for 3-5 minutes and relieved by rest and anti-angina medication. Main goal of treatment is to avoid future episodes and heart attack. Aspirin, Beta blockers, calcium channel blockers, nitroglycerin, ACE inhibitors, statins etc. are usually prescribed but none of these gives freedom from disease.

Myocardial Infarction:

Myocardial Infarction or heart attack occurs when blood supply to a part of heart gets blocked resulting in death of heart cells. Classical symptoms of heart attack are sudden pain, palpitations, sweating, nausea, vomiting etc. Risk factors for myocardial infarction are same as for atherosclerosis such as hypertension, diabetes, obesity, hypercholesterolemia etc. After myocardial Infarction oxygen, aspirin, sublingual Glyceryl Trinitrate and pain reliever such as Morphine Sulfate is given immediately. Besides this treatment, patients of heart attack are advised to take several medicines for long term so that secondary cardiovascular events such as myocardial infarction, congestive heart failure etc. can be prevented. Some of the commonly prescribed drugs are Aspirin, Metoprolol, Statins etc. But ultimately surgery is advised.

Heart Failure:

Heart failure is a disease in which because of problem with structure or function, capacity of heart to supply sufficient blood flow to meet the body requirement is impaired. Common causes of heart failure are hypertension, myocardial infarction etc. Common symptoms of heart failure are shortness of breath, reduced exercise capacity, coughing, ankle swelling etc. Low salt intake and some tolerated exercise is encouraged. Medicines such as beta blockers, ACE inhibitors etc. are prescribed. Surgery is also advised in some cases but none of these treatments are curative.

Stroke:

Stroke is caused by loss of blood supply to the brain resulting in loss of brain functions within minutes, such as inability to move one or more limb(s), inability to understand or formulate speech, inability to see one side of the visual field, numbness, balance problem, altered breathing and heart rate etc. Risk factors for stroke are hypertension, diabetes, obesity, high blood cholesterol level etc. Prevention is the best measure to avoid stroke. Aspirin is given to the patients of myocardial infarction to prevent primary stroke. To prevent secondary stroke blood pressure control, Statins, Aspirin, Dipyridamole, oral anticoagulants etc. are advised. In most cases surgical interventions are required, but still nothing gives freedom from disease.

Paralysis:

Paralysis is caused by damage to the nervous system specially spinal cord resulting in loss of ability to move muscles. Mostly paralysis is caused by stroke, trauma, poliomyelitis, multiple sclerosis, botulism etc. There is no treatment for Paralysis. Usually massage therapy, and physiotherapy is advised.

Cerebral Palsy:

Cerebral palsy refers to a group of non-progressive, motor, non-contagious conditions that causes physical and mental disability in development. Cerebral palsy is caused by damage to the motor control centers of developing brain. Babies born with cerebral palsy have birth defects such as small head, spinal curvature etc. Speech and communication disorders, mental retardation, learning disabilities, sensory impairments etc. are common in people with cerebral palsy. Usually physical therapy, occupational therapy, speech therapy, massage therapy, drugs to control seizures, relax muscle spasm, hyperbaric oxygen, surgery to release tight muscles, orthotic devices, communication aids, rolling walkers etc. are advised depending upon the requirement of the patient. Cord blood therapy is also given to patients. Still cerebral palsy is incurable disorder.

Epilepsy:

Epilepsy is a chronic neurological disorder characterized by recurrent unprovoked seizures, due to abnormal neuronal activity in brain. There are more than 40 different types of Epilepsy such as atonic seizures, benign Rolandic Epilepsy, absence seizures, clonic seizures, frontal lobe Epilepsy, reflex Epilepsy etc. Main treatment of epilepsy is anticonvulsant drugs. In some cases implantation of a stimulator of the Vagus nerve can be helpful. Neurological operations for epilepsy are helpful in reducing frequency and severity of seizures or in some cases can be curative. Inspite of all these advances, epilepsy is still incurable.

Parkinson's Disease:

Parkinson's disease is a chronic and progressive degenerative disorder of central nervous system resulting in impairment of motor skills, speech and other cognitive function of patient. It is characterized by muscle rigidity, tremor, slowing of physical movement, disorders of mood, behavior etc. Usually L-Dopa, Carbidopa, Dopamine agonists, MAO-B inhibitors etc. are prescribed to treat the patients. In some cases, surgery is also advised. Regular physical exercise and/or various types of therapy such as speech therapy are helpful but still there is no cure.

Migraine:

Migraine is a neurological syndrome characterized by unilateral and pulsating headache, nausea, vomiting, altered bodily perceptions such as increased sensitivity to bright light and sound. Cause of migraine attacks is idiopathic but certain triggers are identified such as allergic reactions, bright light, loud noises, physical or emotional stress, skipping meals, changes in sleep pattern etc. Best way to prevent migraine attacks is to avoid triggers. Usually analgesics for headache and anti-emetic for nausea is advised to patients. Nonsteroidal anti-inflammatory drugs are prescribed but none of these treatments gives freedom from disease:

Anxiety:

Anxiety is a psychological and physiological state in which emotional, behavioral and other components combine to create an unpleasant feeling associated with uneasiness, fear etc. Anxiety is a generalized mood condition that occurs without an identifiable triggering stimulus, whereas fear occurs in presence of threat. Anxiety can be accompanied by physical effects such as fatigue, nausea, chest pain, heart palpitations, shortness of breath, headache etc. There is no lasting treatment for Anxiety.

Multiple Myeloma:

Multiple myeloma is cancer of white blood cells which produces antibodies. Because it affects many organs so sign and symptoms vary from patient to patient. Common symptoms are bone pain usually in spine and ribs, renal failure, anemia, neurological symptoms etc. Although multiple myeloma is incurable but still steroids, chemotherapy, thalidomide, stem cell transplantation are advised.

Renal Failure:

Renal failure is disease condition in which kidney fails to function properly resulting in elevation of serum Creatinine because of decrease in glomerular filtration rate. Patients of Renal failure show symptoms of nausea, weight loss, less frequent urination, blood in urine, swelling on legs, ankles, face, hands etc. Dialysis is advised to get rid of accumulated waste products from body. In some cases renal transplant is advised. None of these treatments give freedom from disease.

DETAILED DESCRIPTION OF THE INVENTION

This invention discloses a toxicity free botanical drug formulation and its manufacturing process(es), which is manufactured from plants *Crinum asiaticum* or component(s) thereof and *Crocus sativus* or component(s) thereof for curative treatment of chronic diseases. This botanical drug is administered to human volunteers in a defined manner. In one embodiment volunteers were healthy in another embodiment volunteers were patients having confirmed diagnosis of one or more than one disease(s) or physiologic condition(s). These human volunteers were administered an effective amount of drug for effective time period and kept under observation and follow up.

Explanation of the Terms:

Botanical Drug Formulation:

This invention discloses a toxicity free botanical drug formulation, comprising of 0.01%-99.999% of *Crinurn asiaticum* or component(s) thereof and 0.001%-30% of *Crocus sativus* or component(s) thereof. In this invention addition of plant *Crocus sativus* or component(s) thereof enhances the action of plant *Crinurn asiaticum* or component(s) thereof resulting in faster recovery of human volunteers suffering from chronic disease(s). In this invention component(s) denotes to any component(s) from plants *Crinum asiaticum* and *Crocus sativus,* specific non-limiting examples of components are extract(s), fraction(s), isolated and/or purified molecule(s), phytochemical(s), synthetic analogue of phytochemical(s). In this invention plants *Crinum asiaticum* and *Crocus sativus* include, but not limited to, any one or more than one or any other or each and every variety of plants *Crinum asiaticum* and *Crocus sativus*. In addition to this, plants *Crinum asiaticum* and *Crocus sativus* include, but not limited to, any one or more than one or each and every part of plants *Crinum asiaticum* and *Crocus sativus* including but not limited to be fresh, dehydrated or preserved in some manner. In this invention botanical drug formulation can be in any form specific non-limiting examples of forms are solid, semi-solid, liquid, suspension, paste, powder, tablets, pills, capsules etc. In this invention drug can be given alone or in combination with other additive(s) including but not limited to herb(s) or component(s) thereof, any other biological material(s) or component(s) thereof, any other chemical(s), phytochemical(s), compound(s), mineral(s) etc.

*Crinum Asiaticum:*

*Crinum asiaticum* (Family Amaryllidaceae) is a large plant, it can be more than 5 feet in length. Leaves can be more than 3 feet in length and extend upwards from the central stem. Flowers are white and fragrant. Bulbs are bitter, emetic, diaphoretic, purgative, expectorant, vulnerary, laxative, carminative, anti-helminthic, aphrodisiac, diuretic, nauseant, anti-inflammatory, antipyretic, thermogenic (Vaidyaratnam, P. S. Varier's Arya Vaidya Sala, *Indian Medicinal Plants*, vol. 2, 209). Leaves of *Crinum asiaticum* smeared with castor oil are used for whitlows and other inflammations at the end of toes and finger. Poultice of heated leaves is used for contusions, sprains, fractures, inflamed joints. Decoction of dried leaves is used as a wash for treatment of hemorrhoids. Juice of fresh leaves is instilled in ear to treat earache and other ear complaints. A poultice made from fresh bulb is used for relieving Osteodynia and Rheumatism (Nguyen, Van Dan and Doan, Thi Nhu *Medicinal Plants in Vietnam, World health Organization*, 1989, ISBN 92 9061 1014). Components isolated from *Crinum asiaticum* have shown anti-inflammatory (Samud A M, et. al., *Immunopharmacology*. 1999, 43(2-3): 311-6, Kim Y H, et. al. *J Cosmet Sci.* 2008, 59(5):419-30.), anti tumor (Sun Q, et. al., *Chem Biodivers*. 2009, 6(10):1751-7.) and anti HIV-1 (Min B S, et. al., *Phytother Res.* 2001 September; 15(6):481-6.) activities in in-vitro experiments.

*Crocus Sativus:*

*Crocus sativus* (Family Iridaceae) herb is perennial, ornamental with grass like leaves and purple colored flowers cultivated worldwide. *Crocus sativus* stimulates blood circulation, digestion and appetite. It is carminative, diaphoretic, stimulant, anti-spasmodic, emmenagogue (Jarald E E and Jarald S E, 2007, *In Textbook of Pharmacognosy & Phytochemistry*, CBS Publishers & Distributors, New Delhi, ISBN-81-239-1488-1, pp 372-374). *Crocus sativus* has been shown to be useful in depression (Wang Y, et. al., *J. Nat. Med.* 2010, 64(1), 24-30.), Alzheimer's disease (Akhondzadeh S, et al., *Psychopharmacology*, 2010, 207 (4), 637-643.), premenstrual syndrome (Agha-Hosseini M et. al. *BJOG*. 2008 March; 115 (4), 515-519.) and against experimental autoimmune encephalomyelitis in mice (Ghazavi A, et. al 2009, 1; 12(9):690-5.) In in-vitro studies, its extract causes inhibition of cancer cell lines (Tavakkol-Afshari J, et. al. *Food Chem Toxicol*. 2008, 46(11), 3443-3447).

Toxicity Free:

This denotes a botanical drug formulation which is toxicity free on long term use even for many years altogether. Only about 1% human volunteers reported nauseating feeling for less then one hour if botanical drug is taken empty stomach. No such problem is encountered if the drug is taken orally after meals. If it is taken intranasally then about 2% volunteers reported minor episodes of sneezing. Besides this there are no adverse effects reported by human volunteers, both healthy and patients.

Human Volunteers:

Human volunteers in the age range of 5 months to 85 years were administered with this botanical drug formulation. According to their age human volunteers were divided in three major groups. A—upto 12 years of age, B—Between 13-60 years of age, C—more then 60 years of age. Specific, non-limiting example of human volunteers are in one embodiment they were perfectly healthy in another embodiment they were patients suffering from one or more than one disease(s) or physiologic condition(s) with confirmed diagnosis at least from last one year. Specific, non limiting examples of disease(s) or physiologic condition(s) are Rhinitis, Sinusitis, Asthma, Urticaria, Psoriasis, Vitiligo, Eczema, Allergic conjunctivitis, Food Allergy, Arthritis, Diabetes, Hypertension, Angina pectoris, Myocardial infarction, Cardiac failure, Stroke, Thyroidism, Female infertility, Menstrual disorder, Male infertility, Anxiety, Depression, Epilepsy, Cerebral palsy, Parkinson's Disease, Migraine, Multiple myeloma, Liver cancer, Paralysis, Post menopausal problems and Menstrual disorder.

Administration of the Botanical Drug in a Defined Manner:

Routes of administration of the drug include, but not limited to intranasal, oral, intra-muscular, intravenous, subcutaneous, intra-dermal, topical, trans-dermal, ophthalmic, intra-rectal, intra-peritoneal or any other route which can be used for treatment of patients. During treatment with this botanical drug patients suffering with different disease(s) or physiologic condition(s) are advised to continue to take whatever medicine they are taking and just add this botanical drug in their treatment. Human volunteers are also advised to get the diagnostic tests done if it is required in some diseases. Specific non-limiting examples are human volunteers suffering from diabetes are advised to get blood glucose level tested frequently, human volunteers suffering from hypertension are advised to get their blood pressure checked regularly. Gradually symptoms of disease(s) or physiologic condition(s) reduce in intensity and a point comes when the patients observe that they are not having disease symptoms any more. During this period, patients gradually reduce the intake of other medicine(s) and then stop them completely while continuing with this botanical drug as the only treatment. Once patients feel free of all the diseases symptoms, they are advised to continue taking this botanical drug for additional period of two months. After discontinuation of treatment with the botanical drug, patients were kept under observations with regular follow up. Botanical drug cures chronic disease(s) or physiologic condition(s), as no symptoms of disease(s) or physiologic condition(s) recurred even several years after stopping the treatment.

Effective Amount of the Botanical Drug:

A therapeutically effective amount is an amount sufficient for treating a disease(s) or physiologic condition(s). Such an amount is sufficient to eradicate each and every symptom associated with particular disease(s) or physiologic condition(s). Effective amount may be administered at a given frequency—specific, non-limiting examples are such as about once a week, about twice a week, daily, about twice a day, about four times a day or more.

Effective amount is varied from one patient to another patient depending upon various factors. Specific, non-limiting examples of various factors are age, body weight, length of disease(s) or physiologic condition(s), severity of disease(s) or physiologic condition(s), type of disease(s) or physiologic condition(s).

As the age increases, effective amount of the drug also increases. Specific, non-limiting examples are in one embodiment 21 years old male (body weight 62 Kgs) suffering from Asthma for last 4 years, in another embodiment 40 years old male (body weight 61 Kgs) suffering from Asthma from last 4 years. In above specific, non-limiting example effective amount for 40 years old patient is more than 21 years old.

With increasing body weight, effective amount of the drug also increases. Specific, non-limiting examples are in one embodiment 45 years old female (body weight 52 Kgs) suffering with Arthritis for last 7 years, in another embodiment 44 years old female (body weight 75 Kgs) suffering with Arthritis for last 6 years. In this specific, non-limiting example effective amount for patient having 75 Kgs body weight is more than the patient having 52 Kgs body weight.

As the length of the disease is more, effective amount of the drug required will also be more. Specific, non limiting examples are in one embodiment 23 years old male (body weight 60 Kgs) is suffering with Rhinitis for last 9 years, in another embodiment 22 year old male (body weight 63 Kgs) is suffering with Rhinitis for last 15 months. In this specific, non-limiting example effective amount for patient suffering for last 9 years is more than the one suffering from last 15 months only.

As the severity of the disease is more, effective amount is more. Specific, non-limiting examples are in one embodiment 35 years old male (body weight 60 Kgs) suffering from Asthma from last 10 years using corticosteroids injections at least twice a week, in another embodiment 37 years old male (body weight 65 Kgs) suffering from Asthma from last 12 years using aesthalin inhaler only once a day. In this specific, non-limiting example effective amount for patient using corticosteroid injection is more than the one using aesthalin inhaler only.

Effective amount varies from one disease to another. Specific, non-limiting examples are in one embodiment 42 years old female (body weight 52 Kgs) is suffering from Arthritis from last 4 years, in another embodiment 41 years old female (body weight 49 Kgs) is suffering from Rhinitis from last 6 years. In this specific, non-limiting example effective amount for patient suffering with Arthritis is more than the patient suffering with Rhinitis.

Effective Time Period:

Effective time period is the time sufficient for treating a disease(s) or physiologic condition(s). Such a time period is sufficient to eradicate each and every symptoms associated with a disease(s) or physiologic condition(s).

Effective time period varies from one single day to several years altogether. Specific, non-limiting examples are, patients are administered the botanical drug only without any other supporting medicine, until they regain perfect health without any disease symptoms continuously for 2 months. Then administration of botanical drug is stopped.

Effective time period varies from one patient to another depending upon various factors. Specific, non-limiting examples of factors are age, body weight, length and severity of disease(s) or physiologic condition(s), type of disease(s) or physiologic condition(s).

As the age of the patient is more, effective time period will be more. Specific, non-limiting examples are in one embodiment 32 years old female (body weight 64 Kgs) suffering with Rhinitis for last 8 years, in another embodiment 55 years old female (body weight 62 Kgs) suffering with Rhinitis for last 7 years. In this specific, non-limiting example effective time period for 55 years old female is more than 32 years old female.

As the body weight is more, effective time period will be more. Specific, non-limiting examples are in one embodiment 25 years old female (body weight 65 Kgs) suffering with Migraine for last 4 years, in another embodiment 27 years old female (body weight 48 Kgs) suffering with Migraine for last 5 years. In this specific, non-limiting example, effective time period for patient having 65 Kgs body weight is more than the one having 48 Kgs body weight.

As the length of disease(s) is more, effective time period will be more. Specific, non-limiting examples are in one embodiment 18 years old male (body weight 55 Kgs) is suffering with Rhinitis for last 15 years, in another embodiment 19 years old male (body weight 56 Kgs) is suffering with Rhinitis for last 2 years. In this specific, non-limiting example effective time period for person suffering from last 15 years is more than the one suffering from last 2 years.

As the severity of disease is more effective time period will be more. Specific, non-limiting examples are in one embodiment 60 years old female (body weight 65 Kgs) is suffering with Arthritis, can not walk even 10-20 steps on her own even after taking strong painkillers, in another embodiment 63 years old female (body weight 64 Kgs) is suffering from Arthritis, can walk freely after taking painkillers. In this specific, non-limiting example effective time period for the patient who can not walk even 10-20 steps is more than the one who can walk freely.

Effective time period varies from one disease to another. Specific, non-limiting examples are in one embodiment 35 years old male human volunteer (body weight 59 Kgs) is suffering from Asthma, in another embodiment 34 years old male human volunteer (body weight 61 Kgs) is suffering from Rhinitis. In this specific, non-limiting example effective time period for Asthma patient is more than the one suffering with Rhinitis.

Follow Up and Observation:

Each and every human volunteers, both healthy and patients are advised to come to clinic frequently and regularly, such as once a week or twice a week and observed by the physician. Observations of volunteers and physicians were duly recorded and more botanical drug was given to each and every volunteer for administration. Initially patients are advised to continue with whatsoever treatment(s)/medicine(s) they are taking and just add this botanical drug in their treatment schedule. But during treatment with this botanical drug slowly they give up all other medication(s) and take this botanical drug as only treatment. Specific, non-limiting examples of all other medications are pain killers, corticosteroids etc. At some point in time patients observed that they are not having disease(s) symptoms anymore. At this point patients are advised to continue to take this botanical drug for additional two months.

Curative Treatment:

Curative treatment denotes that the patients get complete freedom from disease(s). Specific, non-limiting examples of complete freedom from disease are as follows, Migraine patients no more have unilateral and pulsating headache, nausea, vomiting, altered bodily perceptions such as increased sensitivity to bright light and sound etc. even several years after stopping the treatment with this botanical drug.

Arthritis patients no more have inflammation and pain in affected joints, even several years after stopping the treatment with this botanical drug.

Paralysis patients are able to move affected parts normally as it was before paralysis, even several years after stopping the treatment with this botanical drug.

Rhinitis patients no more have symptoms of runny nose, nasal congestion and post, nasal drip etc. even several years after stopping the treatment with this botanical drug.

Asthma patients no more have symptoms of night time cough, shortness of breath, tight feeling in the chest etc. even several years after stopping the treatment with this botanical drug.

Epilepsy patients no more have unprovoked seizures and feel healthy, even several years after stopping the treatment with this botanical drug.

Chronic Diseases:

Chronic diseases are the group of diseases which can not be cured by any available treatment. Novelty of this invention is that it discloses a toxicity free botanical drug formulation and its manufacturing process(es) for the curative treatment of chronic diseases. This invention also discloses the method of treatment of patients suffering with various chronic disease(s) or physiologic condition(s). In this invention two routes of inoculation were used and both routes can curatively treat patients. In some patients oral route was used but in other intranasal route was used. But scope of present invention should not be limited to oral and intranasal routes only. Specific, non-limiting examples of treatment of human volunteers (patients) suffering with various chronic disease(s) or physiologic condition(s) are as follows. But scope of present invention should not be limited to following disease(s) or physiologic condition(s) only.

EXAMPLE 1

Treatment of Rhinitis:

Rhinitis is a common chronic disease also identified as runny nose. In this disease nasal mucosa gets inflammed resulting in secretion of excessive mucous thus giving symptoms of runny nose, nasal congestion and post nasal drip. Botanical drug cures Rhinitis, as no symptoms of Rhinitis recurred even several years after stopping the treatment. Table 1 shows the details of human volunteers treated for Rhinitis.

TABLE 1

| Age Range | No. of Patients of Rhinitis | Male/Female | Duration of Treatment (Months) |
|---|---|---|---|
| 5 Months-12 Yrs | 018 | 12/6 | 1-3 + 2 |
| 13 Yrs-59 Yrs | 132 | 85/47 | 1-6 + 2 |
| 64 Yrs-68 Yrs | 004 | 3/1 | 4-7 + 2 |
| Total | 154 | 100/54 | |

EXAMPLE 2

Treatment of Sinusitis:

Chronic Sinusitis is a disease condition in which paranasal sinuses are inflammed. Symptoms of Sinusitis are facial pain, nasal congestion, thick yellow or green nasal discharge, headache, vertigo, feeling of facial fullness, general malaise, fever etc. Botanical drug cures Sinusitis as no symptoms of Sinusitis recurred even several years after stopping the treatment. Table 2 shows the details of human volunteers treated for Sinusitis.

TABLE 2

| Age Range | No. of Patients of Sinusitis | Male/Female | Duration of Treatment (Months) |
|---|---|---|---|
| 5-12 Yrs | 02 | 01/01 | 2-3 + 2 |
| 20-54 Yrs | 16 | 10/06 | 2-5 + 2 |
| 64 | 01 | 01/00 | 10 + 2 |
| Total | 19 | 12/07 | |

EXAMPLE 3

Treatment of Asthma:

Asthma, a chronic disease caused by inflammation of the lungs in which bronchi are reversibly narrowed, common symptoms of Asthma and other lung diseases, such as COPD are night time cough, shortness of breath, tight feeling in the chest etc. Botanical drug cures Asthma, as no symptoms of Asthma, recurred even several years after stopping the treatment. Table 3 shows the details of human volunteers treated for Asthma.

TABLE 3

| Age Range | No. of Patients of Asthma | Male/Female | Duration of Treatment (Months) |
|---|---|---|---|
| 5 Months-12 Yrs | 026 | 21/05 | 01-04 + 2 |
| 13 Yrs-60 Yrs | 168 | 100/68 | 02-23 + 2 |
| 62-85 Yrs | 019 | 10/09 | 06-24 + 2 |
| Total | 213 | 131/82 | |

EXAMPLE 4

Treatment of Urticaria:

Urticaria is a type of skin disease caused by an inflammatory reaction in the skin which results in edema notable as red, raised, itchy bumps. Botanical drug cures Urticaria, as no symptoms of Urticaria recurred even several years after stopping the treatment. Table 4 shows the details of human volunteers treated for Urticaria.

TABLE 4

| Age Range | No. of Patients of Urticaria | Male/Female | Duration of Treatment (Months) |
|---|---|---|---|
| 4-12 Yrs | 11 | 08/03 | 01-14 + 02 |
| 13-60 Yrs | 51 | 26/25 | 01-18 + 02 |
| 62-68 Yrs | 05 | 01/04 | 04-21 + 02 |
| Total | 67 | 35/32 | |

EXAMPLE 5

Treatment of Psoriasis:

Psoriasis is a non-contagious skin disease which affects joints and nails also. This is an autoimmune disease causing inflammation in joints and on skin causing red scaly patches. Botanical drug cures Psoriasis, as no symptoms of Psoriasis recurred even several years after stopping the treatment. Table 5 shows the details of human volunteers treated for Psoriasis.

TABLE 5

| Age Range | No. of Patients of Psoriasis | Male/Female | Duration of Treatment (Months) |
|---|---|---|---|
| 12 Yrs | 01 | 01/00 | 12 + 02 |
| 30-60 Yrs | 08 | 05/03 | 08-24 + 02 |
| Total | 09 | 06/03 | |

EXAMPLE 6

Treatment of Eczema:

Eczema is a chronic disease due to inflammation of epidermis. Common symptoms are skin edema, redness, itching and dryness, crusting, flaking etc. Botanical drug cures Eczema, as no symptoms of Eczema recurred even several years after stopping the treatment. Table 6 shows the details of human volunteers treated for Eczema.

TABLE 6

| Age Range | No. of Patients of Eczema | Male/Female | Duration of Treatment (Months) |
|---|---|---|---|
| 44 & 48 Yrs | 02 | 02/00 | 10 & 24 + 2 |
| Total | 02 | 02/00 | |

EXAMPLE 7

Treatment of Vitiligo:

Vitiligo is a chronic disorder causes depigmentation in skin patches. In this disease Melanocytes are either dead or unable to make skin pigments. Botanical drug cures Vitiligo, as no symptoms of Vitiligo recurred even several years after stopping the treatment. Table 7 shows the details of human volunteers treated for Vitiligo.

TABLE 7

| Age Range | No. of Patients of Vitiligo | Male/Female | Duration of Treatment (Months) |
|---|---|---|---|
| 12 & 30 Yrs | 02 | 01/01 | 29 & 36 + 2 |
| Total | 02 | 01/01 | |

EXAMPLE 8

Treatment of Conjunctivitis:

Chronic allergic Conjunctivitis denotes to inflammation of the conjunctiva, the outermost layer of the eye and the inner surface of eyelids. Common symptom of Conjunctivitis are redness, irritation and watering of eyes. Botanical drug cures Conjunctivitis, as no symptoms of Conjunctivitis recurred even several years after stopping the treatment. Table 8 shows the details of human volunteers treated for Conjunctivitis.

TABLE 8

| Age Range | No. of Patients of Conjunctivitis | Male/Female | Duration of Treatment (Months) |
|---|---|---|---|
| 04-12 Yrs | 05 | 03/02 | 01-04 + 2 |
| 13-60 Yrs | 46 | 26/20 | 01-10 + 2 |
| Total | 51 | 29/22 | |

EXAMPLE 9

Treatment of Food Allergy:

Food allergy is caused by an abnormal reaction to food substances. Mostly allergic reactions have an acute onset and results in symptoms such as skin rashes, nasal congestion, wheezing, shortness of breath, itching and swelling of lips, eyes, tongue, face, nausea, vomiting, abdominal pain and rarely anaphylaxis which results in death. At the start of treatment with this botanical drug human volunteers suffering from Food Allergy are advised not to eat any food which causes Allergy. Botanical drug cures Food Allergy, as no symptoms of Food Allergy recurred after challenge with the food to which patient was allergic, even several years after stopping the treatment. Table 9 shows the details of human volunteers treated for Food Allergy.

TABLE 9

| Age Range | No. of Patients of Food Allergy | Male/Female | Duration of Treatment (Months) |
|---|---|---|---|
| 04-12 Yrs | 07 | 04/03 | 02-06 + 2 |
| 14 Yrs-58 Yrs | 32 | 16/16 | 02-08 + 2 |
| 62-64 Yrs | 02 | 02/00 | 08 & 14 + 2 |
| Total | 41 | 22/19 | |

EXAMPLE 10

Treatment of Arthritis:

Arthritis is a group of chronic diseases involving damage to the body joints. There are more then 100 types of Arthritis—common symptoms of all Arthritis are inflammation and pain in affected joints. Botanical drug cures Arthritis, as no symptoms of Arthritis recurred even several years after stopping the treatment. Table 10 shows the details of human volunteers treated for Arthritis.

TABLE 10

| Age Range | No. of Patients of Arthritis | Male/Female | Duration of Treatment (Months) |
|---|---|---|---|
| 19-60 Yrs | 68 | 25/43 | 06-28 + 2 |
| 62-82 Yrs | 16 | 07/09 | 18-38 + 2 |
| Total | 84 | 32/52 | |

EXAMPLE 11

Treatment of Diabetes:

Diabetes is a chronic disease in which glucose accumulates in the blood and gets excreted in urine giving rise to various disease symptoms such as polyuria, polydipsia etc. Botanical drug cures Diabetes as no symptoms of Diabetes recurred even several years after stopping the treatment. Table 11 shows the details of human volunteers treated for Diabetes.

TABLE 11

| Age Range | No. of Patients of Diabetes | Male/Female | Treatment duration (Months) |
|---|---|---|---|
| 34-58 Yrs | 10 | 06/04 | 06-30 + 02 |
| 66 Yrs | 01 | 01/00 | 28 + 02 |
| Total | 11 | 07/04 | |

EXAMPLE 12

Treatment of Menstrual disorders:

All of the patients in this group had the problem of excessive bleeding and/or irregular Menstrual cycle except one. This one 37 years old female had no Menstrual bleeding for past 2 years. During the course of the treatment with botanical drug she not only gained normal Menstrual cycle but also conceived a baby. Botanical drug cures Menstrual disorder as no symptoms of Menstrual disorder recurred even several years after stopping the treatment. Table 12 shows the details of human volunteers treated for Menstrual disorders.

TABLE 12

| Age Range | No. of Patients of Menstrual disorders | Male/Female | Treatment Duration (Months) |
|---|---|---|---|
| 14-40 Yrs | 09 | 00/09 | 09-20 + 02 |
| Total | 09 | 00/09 | |

EXAMPLE 13

Treatment of Thyroidism:

Thyroidism is a chronic disease caused by abnormal production of thyroid hormones, such as T3, T4, TSH by the thyroid gland. Common symptoms of Thyroidism are fatigue, weight gain, bradycardia, impaired memory etc. Botanical drug cures Thyroidism as no symptoms of Thyroidism recurred even several years after stopping the treatment. Table 13 shows the details of human volunteers treated for Thyroidism.

TABLE 13

| Age Range | No. of Patients of Thyroidism | Male/Female | Treatment Duration (Months) |
|---|---|---|---|
| 17-56 Yrs | 13 | 04/09 | 15-38 + 02 |
| Total | 13 | 04/09 | |

EXAMPLE 14

Treatment of Hypertension:

Hypertension or high blood pressure is a disease condition in which blood pressure is chronically elevated. Continuous hypertension is one of the risk factor for strokes, heart attacks, heart failure, chronic renal failure etc. Mild to moderate hypertension is usually asymptomatic but accelerated hypertension is associated with headache, confusion, nausea, vomiting etc. Botanical drug cures Hypertension. Table 14 shows the details of human volunteers treated for Hypertension.

TABLE 14

| Age Range | No. of Patients of Hypertension | Male/Female | Duration of Treatment (Months) |
|---|---|---|---|
| 20-54 Yrs | 20 | 11/09 | 08-22 + 02 |
| 61-74 Yrs | 05 | 02/03 | 09-28 + 02 |
| Total | 25 | 13/12 | |

EXAMPLE 15

Treatment of Cardiac Disorders:

Cardiac disorders are of various types. Specific, non-limiting examples are Angina pectoris, myocardial infarction, heart failure, Stroke etc. Treatment was curative in nature as no Cardiac disease symptoms recurred even several years after stopping the treatment. Table 15 shows the details of human volunteers treated for Cardiac disorders.

TABLE 15

| Age Range | No. of Patients of Cardiac Disorders | Male/Female | Duration of Treatment (Months) |
|---|---|---|---|
| 4-70 Yrs | 6 | 03/03 | 10-60 + 2 |
| Total | 6 | 03/03 | |

EXAMPLE 16

Treatment of Migraine:

Migraine is a neurological syndrome characterized by unilateral and pulsating headache, nausea, vomiting, altered bodily perceptions such as increased sensitivity to bright light, sounds etc. Botanical drug cures Migraine, as no symptoms of Migraine recurred even several years after stopping the treatment. Table 16 shows the details of human volunteers treated for Migraine.

TABLE 16

| Age Range | No. of Patients of Migraine | Male/Female | Treatment Duration (Months) |
|---|---|---|---|
| 04-12 Yrs | 08 | 04/04 | 04-10 + 2 |
| 14-60 Yrs | 75 | 25/50 | 04-24 + 2 |
| 64 & 65 Yrs | 02 | 01/01 | 12 & 14 + 2 |
| Total | 85 | 30/55 | |

EXAMPLE 17

Treatment of Epilepsy:

Epilepsy is a chronic neurological disorder characterized by recurrent unprovoked seizures, due to abnormal neuronal activity in brain leading to abnormal development of patients. Botanical drug cures Epilepsy, as no symptoms of Epilepsy recurred even several years after stopping the treatment. Table 17 shows the details of human volunteers treated for Epilepsy.

TABLE 17

| Age Range | No. of Patients of Epilepsy | Male/Female | Duration of Treatment (Months) |
|---|---|---|---|
| 01-17 Yrs | 14 | 10/04 | 12-48 + 2 |
| Total | 14 | 10/04 | |

EXAMPLE 18

Treatment of Cerebral Palsy:

Patients suffering from cerebral Palsy commonly have learning disabilities, sensory impairments, mental retardation, speech and communication disorders etc. Botanical drug cures Cerebral Palsy, as no symptoms of Cerebral Palsy recurred even several years after stopping the treatment. Table 18 shows the details of human volunteers treated for Cerebral Palsy.

TABLE 18

| Age Range | No. of Patients of Cerebral Palsy | Male/Female | Duration of Treatment (Months) |
|---|---|---|---|
| 02-19 Yrs | 14 | 10/04 | 24-84 + 2 |
| Total | 14 | 10/04 | |

EXAMPLE 19

Treatment of Parkinson's Disease:

Common Symptoms of Parkinson's disease are muscle rigidity, tremor, slowing of physical movement, disorders of mood etc. Botanical drug cures Parkinson's disease, as no symptoms of Parkinson's disease recurred even several years after stopping the treatment. Table 19 shows the details of human volunteers treated for Parkinson's disease.

TABLE 19

| Age Range | No. of Patients of Parkinson's disease | Male/Female | Duration of Treatment (Months) |
|---|---|---|---|
| 50 & 74 Yrs | 02 | 00/02 | 36 & 60 + 2 |
| Total | 02 | 00/02 | |

EXAMPLE 20

Treatment of Paralysis:

Paralysis is caused by damage to the nervous system, resulting in loss of ability to move muscles. Botanical drug cures Paralysis, as no symptoms of Paralysis recurred even several years after stopping the treatment. Table 20 shows the details of human volunteers treated for Paralysis.

TABLE 20

| Age Range | No. of Patients of Paralysis | Male/Female | Duration of Treatment (Months) |
|---|---|---|---|
| 30-74 Yrs | 05 | 03/02 | 06-48 + 2 |
| Total | 05 | 03/02 | |

EXAMPLE 21

Treatment of Neurological Disorders:

Other neurological disorders were minor. Specific, non-limiting examples are stammering, fear, numbness, bedwetting, unable to hold pen, anxiety, depression, tremors, slight memory loss, unclear speech etc. Botanical drug cures other minor Neurological disorders, as no symptoms of these recurred even several years after stopping the treatment. Table 21 shows the details of human volunteers treated for other minor Neurological disorders.

TABLE 21

| Age Range | No. of Patients of Neurological disorders | Male/Female | Duration of Treatment (Months) |
|---|---|---|---|
| 01-53 Yrs | 17 | 12/05 | 01-42 + 2 |
| Total | 17 | 12/05 | |

EXAMPLE 22

Treatment of Multiple Myeloma:

Multiple myeloma is a cancer of white blood cells, which produces antibodies. Because it affects many organs so sign and symptoms vary from patient to patient. Common symptoms are bone pain usually in spine and ribs, renal failure, anemia, neurological symptoms etc. Botanical drug cures Multiple myeloma, as no symptoms of Multiple myeloma recurred even several years after stopping the treatment. Table 22 shows the details of human volunteer treated for Multiple Myeloma.

TABLE 22

| Age Range | No. of Patients of Multiple Myeloma | Male/Female | Duration of Treatment (Months) |
|---|---|---|---|
| 60 Yrs | 01 | 01/00 | 48 + 2 |
| Total | 01 | 01/00 | |

We claim:

1. A composition for treating a chronic inflammatory disease in a human in need thereof consisting essentially of therapeutically effective amounts of *Crinum asiaticum* extract, *Crocus sativus* extract and at least one excipient.

2. The composition of claim 1, wherein said *Crinum asiaticum* extract is present in an amount of about 0.001% to about 99.999% and said *Crocus sativus* extract is present in an amount of about 0.001 to about 30% of the composition.

3. The composition of claim 1, wherein said composition is in a form selected from the group consisting of solid, semi-solid, liquid, suspension, paste, powder, tablet, pill and capsule.

4. The composition of claim 1, wherein said composition is formulated to be administered orally, intramuscularly, intravenously, subcutaneously, intradermally, topically, transdermally, rectally, intraperitoneally, or through contact with the eye.

* * * * *